(12) United States Patent
Iso et al.

(10) Patent No.: US 9,310,343 B2
(45) Date of Patent: Apr. 12, 2016

(54) COLUMN OVEN

(75) Inventors: Keisuke Iso, Kyoto Pref. (JP); Takao Okado, Kyoto Pref. (JP)

(73) Assignee: SHIMADZU CORPORATION, Kyoto (JP)

( * ) Notice: Subject to any disclaimer, the term of this patent is extended or adjusted under 35 U.S.C. 154(b) by 489 days.

(21) Appl. No.: 13/031,580

(22) Filed: Feb. 21, 2011

(65) Prior Publication Data

US 2011/0290233 A1 Dec. 1, 2011

(30) Foreign Application Priority Data

May 31, 2010 (JP) ................................. 2010-124915

(51) Int. Cl.
*A21B 1/00* (2006.01)
*C02F 11/18* (2006.01)
*G01N 30/30* (2006.01)
*G01N 30/54* (2006.01)
*G01N 27/447* (2006.01)

(52) U.S. Cl.
CPC ........ *G01N 30/30* (2013.01); *G01N 2030/3084* (2013.01)

(58) Field of Classification Search
None
See application file for complete search history.

(56) References Cited

U.S. PATENT DOCUMENTS

| | | | | |
|---|---|---|---|---|
| 4,223,385 A | * | 9/1980 | Miller et al. | 700/210 |
| 4,275,708 A | * | 6/1981 | Wood | 126/355.1 |
| 5,083,450 A | * | 1/1992 | Grindstaff | 73/23.25 |
| 5,258,601 A | * | 11/1993 | Takano | 219/486 |
| 5,575,194 A | * | 11/1996 | Maher et al. | 99/330 |
| 5,716,842 A | * | 2/1998 | Baier et al. | 435/283.1 |
| 5,778,681 A | * | 7/1998 | Li et al. | 62/50.2 |
| 5,965,410 A | * | 10/1999 | Chow et al. | 435/91.2 |
| 6,103,112 A | * | 8/2000 | Sutton et al. | 210/198.2 |
| 6,120,667 A | * | 9/2000 | Hayashizaki et al. | 204/603 |
| 6,172,346 B1 | * | 1/2001 | Wroe | 219/681 |
| 6,225,061 B1 | * | 5/2001 | Becker et al. | 506/16 |

(Continued)

FOREIGN PATENT DOCUMENTS

| | | |
|---|---|---|
| CN | 1756952 A | 4/2006 |
| CN | 1963499 A | 5/2007 |

(Continued)

OTHER PUBLICATIONS

"First Office Action of China Counterpart Application", issued on Jul. 1, 2013, with English translation thereof, p. 1-p. 12.

(Continued)

*Primary Examiner* — Gregory Huson
*Assistant Examiner* — Eric Gorman
(74) *Attorney, Agent, or Firm* — J.C. Patents (57) ABSTRACT

A column oven that may enable a heat block to provide the best temperature distribution, and increase temperature evenness of a column is provided. In a column oven 400 that heats or cools a heat block 10 contacting a column 40 and adjusts temperature of the column 40 through heat transmission from the heat block 10, a plurality of temperature adjustment bodies 21 and 22 is separately disposed along the longitudinal direction of the heat block 10, and heats or cools the heat block 10, a plurality of temperature sensors 31 and 32 measuring the temperatures of the heat block 10 adjacent to the temperature adjustment bodies 21 and 22 is also disposed, and the corresponding temperature adjustment bodies 21 and 22 are controlled independently according to the temperatures measured by the temperature sensors 31 and 32.

3 Claims, 10 Drawing Sheets is a schematic view of a configuration of heaters 21, 22 and temperature sensors 31, 32 on a heat block 10

(56) References Cited

U.S. PATENT DOCUMENTS

| | | | |
|---|---|---|---|
| 6,355,165 B1* | 3/2002 | Sutton et al. | 210/198.2 |
| 6,372,142 B1* | 4/2002 | Gjerde et al. | 210/635 |
| 6,475,388 B1* | 11/2002 | Gjerde et al. | 210/635 |
| 6,550,961 B1* | 4/2003 | Ueda | 374/44 |
| 6,576,133 B2* | 6/2003 | Gjerde et al. | 210/635 |
| 6,616,849 B1* | 9/2003 | Osajima et al. | 210/750 |
| 6,652,745 B2* | 11/2003 | Gjerde et al. | 210/198.2 |
| 6,929,731 B2 | 8/2005 | Foret et al. | |
| 8,323,570 B2* | 12/2012 | Johnson et al. | 422/82.01 |
| 2001/0042714 A1* | 11/2001 | Gjerde et al. | 210/634 |
| 2002/0153312 A1* | 10/2002 | Gjerde et al. | 210/635 |
| 2002/0179594 A1* | 12/2002 | Hada et al. | 219/494 |
| 2003/0165941 A1* | 9/2003 | Gjerde et al. | 435/6 |
| 2004/0089654 A1* | 5/2004 | Kitano et al. | 219/601 |
| 2005/0139076 A1* | 6/2005 | Ledford, Jr. | 96/102 |
| 2005/0145614 A1* | 7/2005 | Wu et al. | 219/390 |
| 2006/0054558 A1* | 3/2006 | Jones et al. | 210/656 |
| 2006/0108350 A1* | 5/2006 | Yamauchi | 219/494 |
| 2007/0074766 A1* | 4/2007 | Klee et al. | 137/487.5 |
| 2007/0107675 A1 | 5/2007 | Kurano | |
| 2007/0289589 A1* | 12/2007 | McFarland | 126/502 |
| 2009/0171862 A1* | 7/2009 | Harrod et al. | 705/412 |
| 2009/0173146 A1* | 7/2009 | Pursch et al. | 73/61.52 |
| 2009/0320829 A1* | 12/2009 | Aitken | 126/587 |
| 2010/0154891 A1* | 6/2010 | Evans | B01J 8/0045 137/2 |
| 2015/0059450 A1* | 3/2015 | Takahashi | G01N 30/30 73/61.53 |

FOREIGN PATENT DOCUMENTS

| | | |
|---|---|---|
| CN | 101622535 A | 1/2010 |
| JP | 03-118619 | 5/1991 |
| JP | 10-104214 | 4/1998 |
| JP | 2000-111536 | 4/2000 |
| JP | 2003-047839 | 2/2003 |
| JP | 2005-140505 | 6/2005 |
| JP | 2009-121937 | 6/2009 |
| JP | 2010-048554 | 3/2010 |

OTHER PUBLICATIONS

"Office Action of Japan Counterpart Application", issued on Jan. 31, 2014, pp. 1-5, with English translation thereof.

* cited by examiner

FIG. 1(a) is a schematic view of a configuration of heaters 21, 22 and temperature sensors 31, 32 on a heat block 10

FIG. 1(b) is a diagram of the temperature distribution of a configuration of heaters 21, 22 and temperature sensors 31, 32 on a heat block 10

FIG. 2(a) is a schematic view of a configuration of heaters 21, 22 and temperature sensors 31, 32 on a heat block 10

FIG. 2(b) is a diagram of the temperature distribution of the heat block 10 and a column 40 when the temperature at the influx side and the outflux side are the same FIG. 3(a) is a schematic view of a configuration of heaters 21, 22 and temperature sensors 31, 32 on a heat block 10

FIG. 3(b) is a diagram of the temperature distribution of the heat block 10 and a column 40 when the setting temperature T2set of heater 22 at the influx side is higher than the setting temperature T1set of heater 21 at the outflux side FIG. 4(a) is a schematic view of a configuration of heaters 21, 22 and temperature sensors 31, 32 on a heat block 10

FIG. 4(b) is a diagram of the temperature distribution of the heat block 10 and a column 40 when the setting temperature T2set of heater 22 at the influx side is too high

FIG. 5(a) is a schematic view of a configuration of heaters 21, 22 and temperature sensors 31, 32 on a heat block 10

FIG. 5(b) is a diagram of the temperature distribution of the heat block 10 and a column 40 when a critical value ΔTmax of the setting temperature difference is set for the setting temperature T2set of the heater 22 at the influx side

FIG 9(a) is a schematic view of a conventional column cooling on a heat block 10 configured with a Peltier Element 53 and a temperature sensor 31

FIG 9(b) is a diagram of the temperature distribution of a conventional column cooling on a heat block 10 configured with a Peltier Element 53 and a temperature sensor 31

FIG. 10(a) is a schematic view of a configuration of Peltier Elements 51, 52 and temperature sensors 31, 32 on a heat block 10

FIG. 10(b) is a diagram of the temperature distribution of the heat block 10 and a column 40 when the setting temperature T2set of Peltier Elements 52 at the influx side is lower than the setting temperature T1set of Peltier Elements 51 at the outflux side FIG 11(a) is a schematic view of a conventional column temperature adjustment on a heat block 60 configured with a heater 71 and a temperature sensor 81 at the center FIG 11(b) is a diagram of the temperature distribution of a conventional column temperature adjustment on a heat block 60 configured with a heater 71 and a temperature sensor 81 at the center FIG 12(a) is a schematic view of a conventional column temperature adjustment on a heat block 60 configured with a heater 71 and a temperature sensor 81 at the influx side FIG 12(b) is a diagram of the temperature distribution of a conventional column temperature adjustment on a heat block 60 configured with a heater 71 and a temperature sensor 81 at the influx side FIG. 13(a) (PRIOR ART)

FIG. 13(b) (PRIOR ART)

COLUMN OVEN

CROSS-REFERENCE TO RELATED APPLICATION

This application claims the priority benefit of Japan patent application serial no. 2010-124915, filed on May 31, 2010. The entirety of the above-mentioned patent application is hereby incorporated by reference herein and made a part of the specification.

BACKGROUND OF THE INVENTION

1. Field of the Invention

The present invention relates to a column oven for adjusting temperature of a column used in a Liquid Chromatograph (LC), and in particular, to a column oven in a heat block manner.

2. Description of Related Art

In the analysis of the LC, an ingredient retention property of the column may be influenced by temperature, and in addition, viscosity of the mobile phase may also be influenced by the temperature; hence, maintaining a constant column temperature is important for realizing high analysis reproducibility. Furthermore, in order to ensure the identity of obtained analysis results (chromatogram) of the same sample by using a plurality of LC devices, to properly control the column temperature is important. Accordingly, in the LC analysis (especially in the analysis of the current mainstream High Performance Liquid Chromatograph (HPLC)), a column oven is usually used to adjust the temperature of the column (referring to Patent Documentation 1).

Figures 11A, 11B:
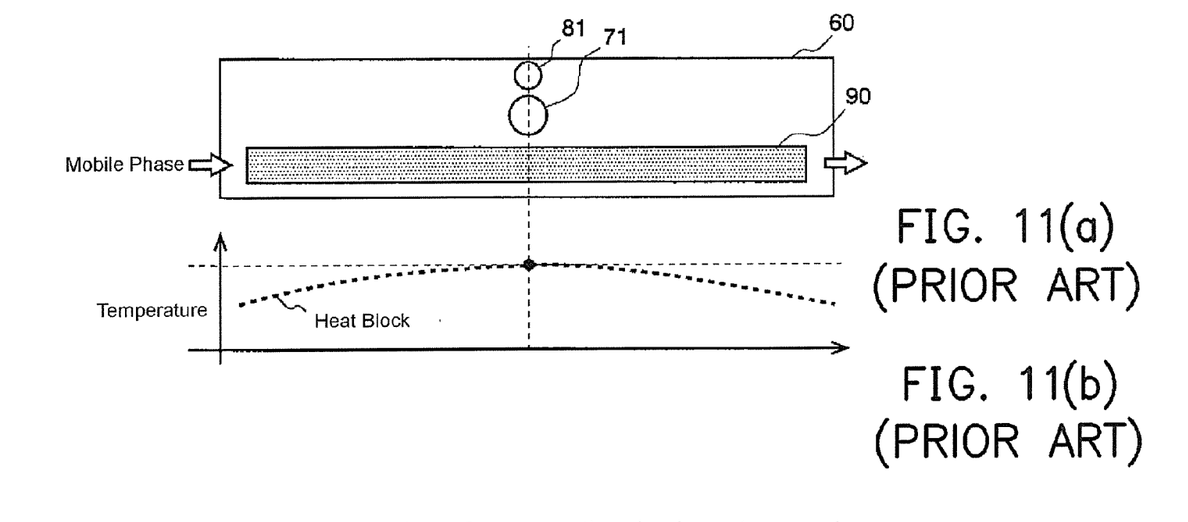
FIG. 11(a) is a schematic view of a configuration of a heater and a temperature sensor on a heat block.
FIG. 11(b) is a diagram of the temperature distribution of the heat block.

The manner for adjusting the temperature of the column oven mainly includes a heat block manner, an air circulation manner, and a liquid circulation manner. As shown in FIG. 11(a), the heat block manner is as follows: allowing a block including aluminum and other metals having high thermal conductivity (a heat block 60) to contact a column 90, and adjusting the temperature of the heat block 60 by using a heater 71 (for example, referring to Patent Documentation 1).

When the heat block manner is used to adjust the temperature of the column oven, the following control is performed. The current temperature of the heat block 60 is measured by using a temperature sensor 81 installed near the heater 71, and the electrical power provided for the heater 71 is adjusted according to the current temperature.

PRIOR TECHNICAL DOCUMENTATION

Patent Documentation

Patent Documentation 1: JP Patent Publication No. 2000-111536

Figures 12A, 12B:
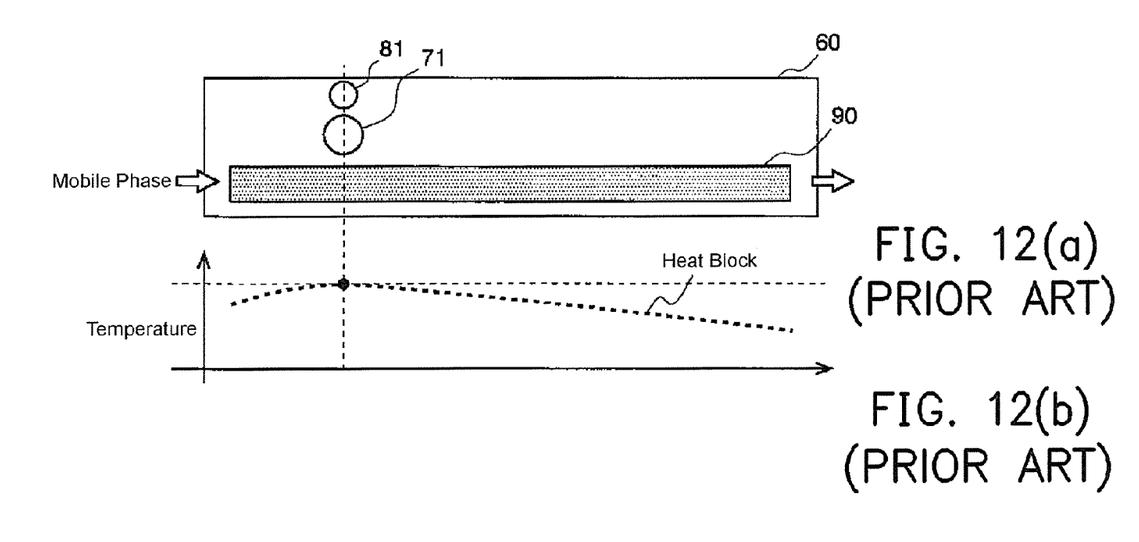
FIG. 12(a) is a schematic view of a configuration of a heater and a temperature sensor on a heat block.
FIG. 12(b) is a diagram of the temperature distribution of the heat block.

In the conventional column oven in the heat block manner, as shown in FIG. 11(a) or 12(a), the temperature is adjusted through a set of heater 71 and temperature sensor 81 installed in the centre or at the left or the right side of the heat block 60. Therefore, as shown in FIG. 11(b) or 12(b), temperature unevenness is generated along the longitudinal direction (the circulation direction of the mobile phase), such that the closer to the installation location of the heater 71, the higher the temperature of the heat block 60, and the farther to the installation location of the heater, the lower the temperature of the heat block 60. Accordingly, the temperature unevenness along the longitudinal direction the column 90 is also generated using the heat block 60 to adjust the temperature.

Figure 13A:
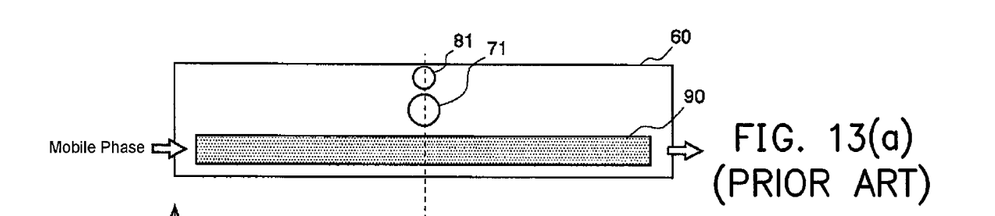
FIG. 13(a) is a schematic view of a configuration of a heater and a temperature sensor on a heat block.
Figure 13B:
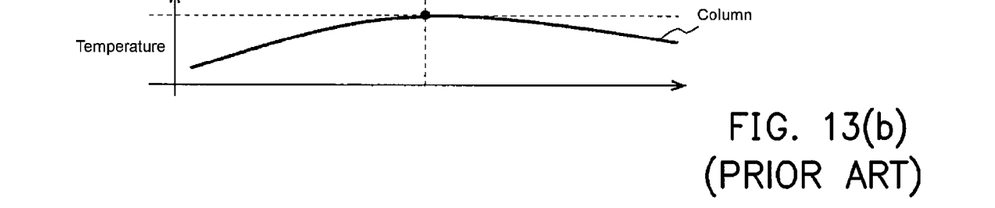
FIG. 13(b) is a diagram of the temperature distribution of a column.

Furthermore, in the process of performing LC analysis, the mobile phase liquid always flows along the column 90, and at this time, the mobile phase with the temperature being non-adjusted (relatively low-temperature) flows into an influx side of the column 90. Therefore, as shown in FIG. 13(b), at the outflux side and the influx side of the column 90, there is a big difference in the column temperature.

In this way, in the conventional column oven in the heat block manner, the temperature unevenness is easily generated along the longitudinal direction of the column, hence, it is difficult to ensure a stable retention time (maintaining time), and to improve the precision of the analysis is thereby hindered.

SUMMARY OF THE INVENTION

Accordingly, the present invention is directed to a column oven, enabling a heat block to provide the best temperature distribution, and improving temperature evenness of the column.

According to the present invention, the column oven for solving the above problem heats or cools the heat block contacting the column, uses heat transmission from the heat block to adjust the temperature of the column. The column oven includes:

a) a plurality of temperature adjustment bodies, separately disposed along the longitudinal direction of the heat block, and heating or cooling the heat block;

b) a plurality of temperature sensors, measuring the temperatures of the heat block adjacent to the temperature adjustment bodies; and c) a control unit, controlling the corresponding temperature adjustment bodies independently according to the temperatures measured by the temperature sensors.

Figures 1A, 1B:
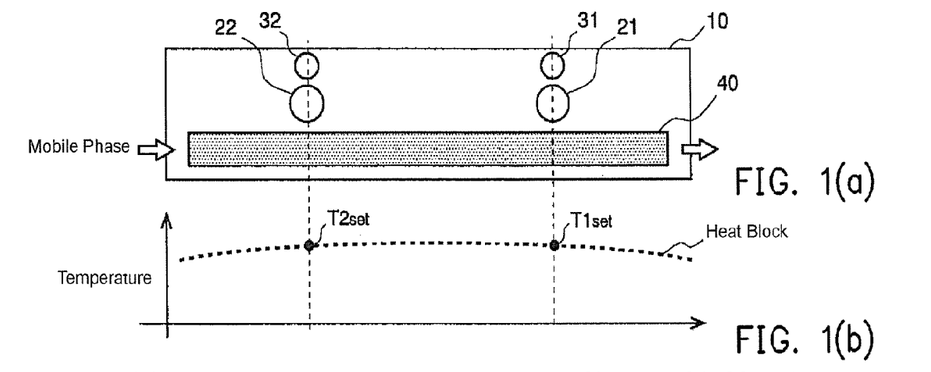
FIG. 1(a) is a schematic view of a configuration of a heater and a temperature sensor on a heat block.
FIG. 1(b) is a diagram of the temperature distribution of the heat block.

According to the present invention, in the column oven, for example, as shown in FIG. 1(a), a plurality of heaters 21 and 22 is disposed on the heat block 10, and the heaters 21 and 22 are separately controlled according to temperature measured by the temperature sensors 31 and 32 installed near the heaters 21 and 22. Therefore, the best temperature distribution (for example, the even temperature distribution as shown in FIG. 1(b)) of the heat block 10 may be formed.

Furthermore, a situation of heating the heat block is illustrated as an example, but the present invention may also be applied to a situation of cooling the heat block by using a Peltier Element. Furthermore, FIGS. 1(a) and 1(b) show an example that two sets of temperature adjustment bodies and temperature sensors are disposed on the heat block 10, and a configuration of three or more temperature adjustment bodies and temperature sensors may also be provided.

The ideal column oven of the present invention further includes:

d) a temperature determination unit respectively determining the setting temperatures of the temperature adjustment bodies according to an analysis condition that at least includes the temperature of the column oven and the flow of the mobile phase applied in the analysis; and the control unit preferably controls the temperature adjustment bodies in a manner of enabling the temperatures measured by the temperature sensors to be the setting temperatures of the temperature adjustment bodies.

Therefore, the temperature adjustment bodies can be controlled according to the best setting temperatures corresponding to the analysis condition of the temperature of the column oven or the flow of the mobile phase.

According to the column oven of the present invention, preferably the temperature determination unit determines the setting temperatures of the temperature adjustment bodies in the following manner that: when the heat block is heated through the plurality of temperature adjustment bodies, the setting temperature is higher for the temperature adjustment body disposed nearer to the influx of the column.

Figures 2A, 2B:
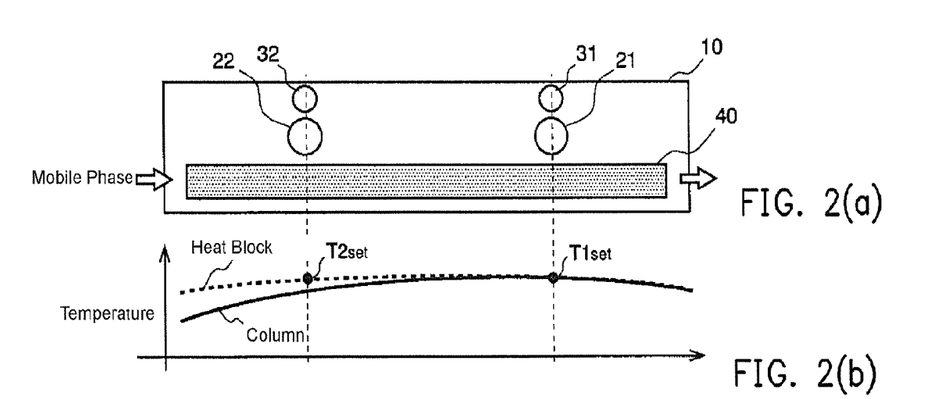
FIG. 2(a) is a schematic view of a configuration of a heater and a temperature sensor on a heat block.
FIG. 2(b) is a diagram of the temperature distribution of the heat block and a column.
Figures 3A, 3B:
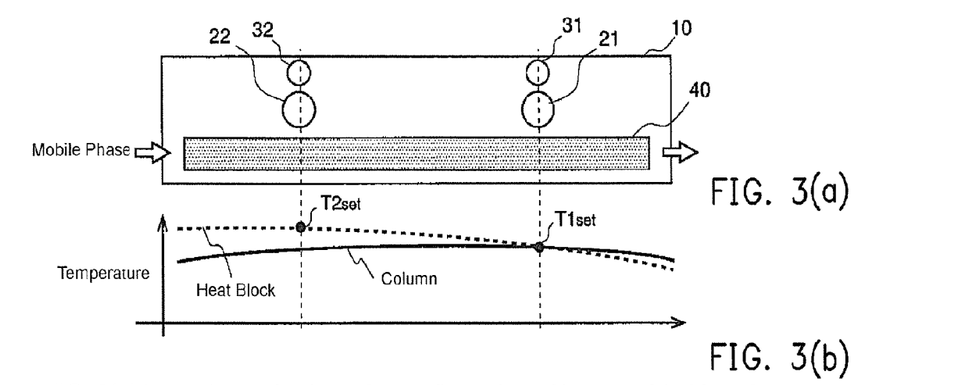
FIG. 3(a) is a schematic view of a configuration of a heater and a temperature sensor on a heat block.
FIG. 3(b) is a diagram of the temperature distribution of the heat block and a column.

Generally, the mobile phase with the temperature not being adjusted flows into the influx of the column, the heat captured by the mobile phase at the influx side becomes more. Therefore, when the same manner is used to heat the vicinity of the influx and other parts, a situation that the column temperature at the influx side being lower (FIGS. 2(a) and 2(b)) exists. Comparatively speaking, in the column oven of the present invention including the aforementioned configuration, for example, as shown in FIGS. 3(a) and 3(b), more heat is provided to the vicinity of the influx of the column 40 by enabling the setting temperature T2set of the heater 22 disposed at the influx side to be higher than the setting temperature T1set of the heater 21 disposed at the outflux side. Therefore, the falling of the column temperature at the vicinity of the influx may be prevented, and the whole column is provided with an even temperature distribution as shown in FIG. 3(b).

Moreover, in the column oven of the present invention, the temperature determination unit determines the setting temperatures of the temperature adjustment bodies in the following manner that: when the heat block is cooled through the plurality of temperature adjustment bodies, the setting temperature becomes lower for the temperature adjustment body disposed nearer to the influx of the column.

Furthermore, in one preferred column oven of the present invention, the temperature determination unit derives a critical value of a setting temperature difference of the temperature adjustment bodies according to the analysis condition, and determines the setting temperatures of the temperature adjustment bodies in a manner such that the setting temperature difference of the temperature adjustment bodies is smaller than the critical value.

Figure 4A:
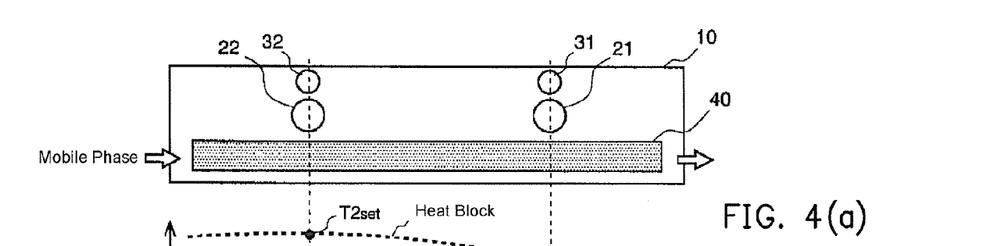
FIG. 4(a) is a schematic view of a configuration of a heater and a temperature sensor on a heat block.
Figure 4B:
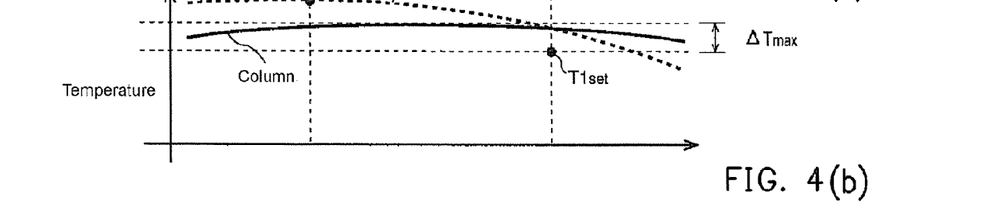
FIG. 4(b) is a diagram of the temperature distribution of the heat block and a column.
Figure 5A:
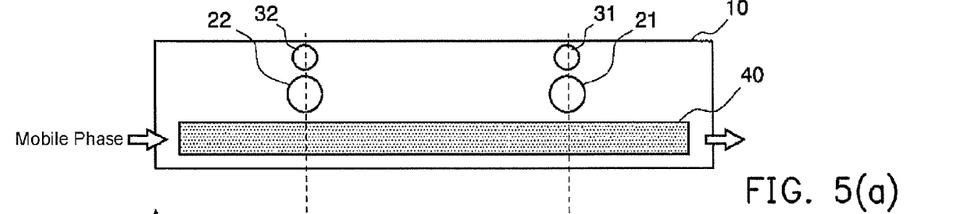
FIG. 5(a) is a schematic view of a configuration of a heater and a temperature sensor on a heat block.
Figure 5B:
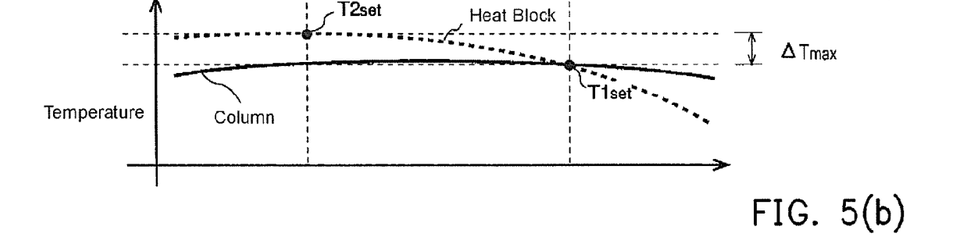
FIG. 5(b) is a diagram of the temperature distribution of the heat block and a column.

For example, in the example shown in FIGS. 3(a) and 3(b), if the setting temperature T2set of the heater at the influx side is too high, the heat provided for the heat block 10 by the heater 22 at the influx side is transmitted to the outflux side through the heat block 10 or the column 40, as shown in FIG. 4(b), block temperature at the outflux side may become higher than the setting temperature T1set of the heater at the outflux side. In this situation, even if the power supply of the heater 21 at the outflux side is adjusted, the measured temperature of the temperature sensor 31 at the outflux side can not become the setting temperature T1set. Therefore, in the column oven of the present invention including the aforementioned construction, as shown in FIGS. 5(a) and 5(b), a critical value ΔTmax of the setting temperature difference of the temperature of the heater 10 at the outflux side not higher than the setting temperature is derived in advance, and then the setting temperature of the temperature adjustment bodies at the outflux side and influx side is determined according to the critical value ΔTmax. Moreover, when the column is cooled, a critical value ΔTmax of the setting temperature difference of the temperature of the heat block at the outflux side not lower than the setting temperature T1 set is derived in advance, and then the setting temperature of the temperature adjustment bodies at the outflux side and the influx side is determined according to the critical value ΔTmax.

Furthermore, in one preferred column oven of the present invention, the temperature determination unit further includes at least any one of the room temperature, the specific heat of the mobile phase, the thermal conductivity of the mobile phase, the diameter of the column, the type of the filler of the column, the length of the column to be the analysis condition to determine the setting temperatures of the plurality of temperature adjustment bodies.

The temperature adjustment may be more appropriately controlled by considering various analysis conditions in this manner.

Beneficial Effect

According to the column oven of the present invention as described above, the heat block may provide the best temperature distribution, and the temperature evenness along the longitudinal direction of the column, in which the temperature thereof is adjusted through the heat block, may be improved. In this way, sample ingredients in the separation column may be stably separated, and the reproducibility of the LC analysis is improved.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 1(a) and 1(b) are diagrams illustrating a column oven of the present invention, wherein

FIGS. 2(a) and 2(b) are diagrams illustrating that the column temperature falls at an influx side, wherein

FIGS. 3(a) and 3(b) are diagrams illustrating an example of increasing setting temperature at an influx side, wherein

FIGS. 4(a) and 4(b) are diagrams illustrating a situation that block temperature at an outflux side exceeds setting temperature, wherein

FIGS. 5(a) and 5(b) are diagrams illustrating an example of setting a critical value for a setting temperature difference between an outflux side and an influx side, wherein

FIGS. 7(a) to 7(d) are views illustrating a heat block according to an embodiment, wherein FIG. 7(a) is a top view.

FIGS. 9(a) and 9(b) are diagrams illustrating a conventional column oven using a Peltier Element to cool.

FIGS. 10(a) and 10(b) are diagrams illustrating a column oven of the present invention using a plurality of Peltier Elements to cool.

FIGS. 11(a) and 11(b) are diagrams illustrating a conventional column oven, wherein

FIGS. 12(a) and 12(b) are diagrams illustrating a conventional column oven according to another embodiment, FIGS. 13(a) and 13(b) are diagrams illustrating that column temperature falls at an influx side in a conventional column oven.

DESCRIPTION OF THE EMBODIMENTS

Figure 6:
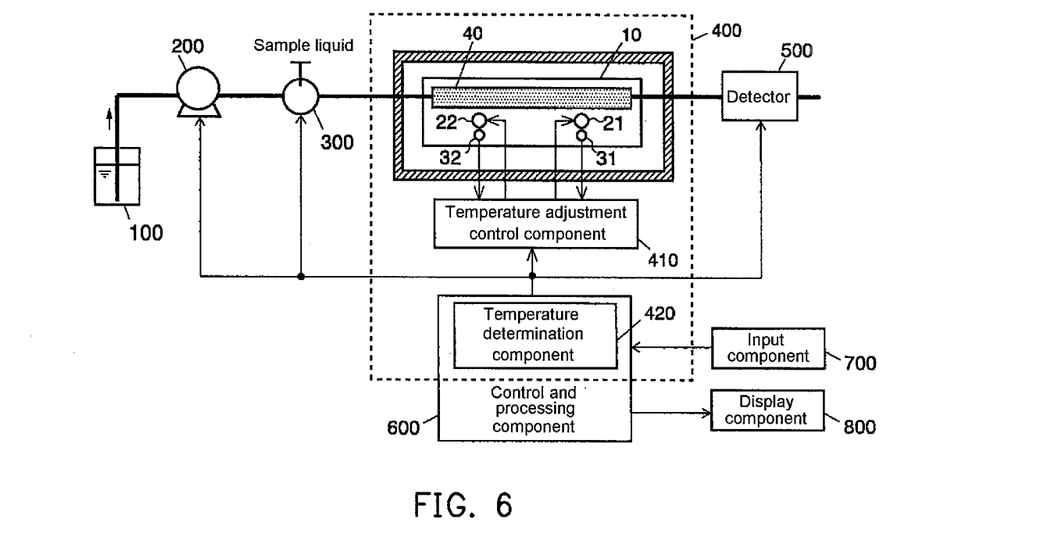
FIG. 6 is a schematic structural view of an LC device including a column oven according to an embodiment of the present invention.
Figure 7A:
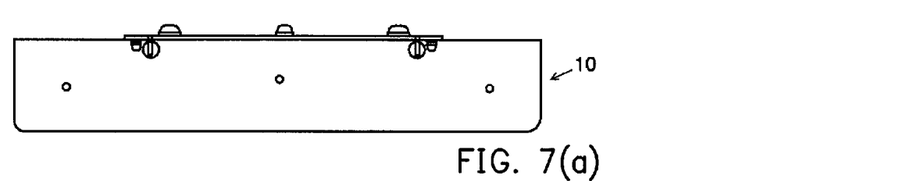
Figure 7B:
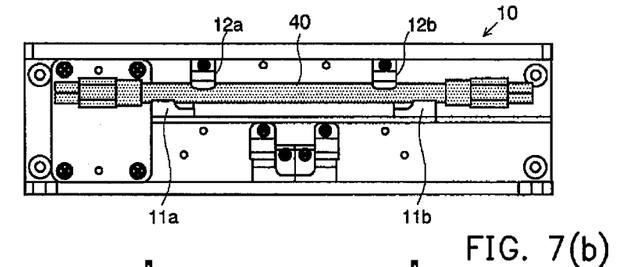
FIG. 7(b) is a front view.
Figure 7C:
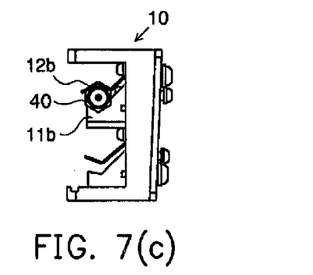
FIG. 7(c) is a side view.
Figure 7D:
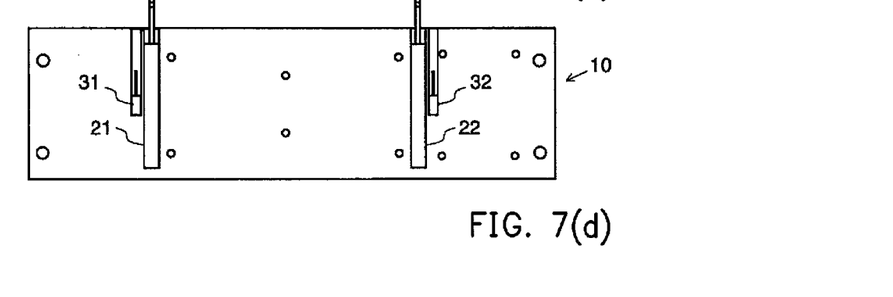
FIG. 7(d) is a rear view.

Reference will now be made in detail to the present embodiments of the invention, examples of which are illustrated in the accompanying drawings. Wherever possible, the same reference numbers are used in the drawings and the description to refer to the same or like parts. A column oven of an embodiment of the present invention is described with reference to the accompanying drawings. FIG. 6 is a structural view of main parts of an LC device of a column oven of this embodiment.

In the LC device, a liquid delivery pump 200 sucks a mobile phase deposited in a mobile phase container 100, and provides the mobile phase to a column 40 with a fixed flow through an automatic sampler 300. The automatic sampler 300 includes an injector that selects a specified sample from a plurality of samples prepared in advance and injects the specified sample into the mobile phase. The injected sample attaches to the mobile phase and is imported into the column 40, and is eluted after separation at the time direction when the injected sample passes through the column 40. The column 40 is received in the column oven 400, eluent from the column is imported into a detector 500 such as an absorption spectrophotometer, and detection signals corresponding to various sample ingredients in the eluent are acquired as time passes.

A heat block 10 as shown in FIGS. 7(a) to 7(d) is disposed in the column oven 400. The heat block 10 is a block made of metal of good thermal conductivity with a section roughly in a "⊐" shape, and support blocks 11a and 11b and leaf springs 12a and 12b are disposed in a depressed space in the "⊐" shape. A groove used for embedding the column 40 is formed on upper surfaces of the support blocks 11a and 11b, and the column 40 is clamped up and down through the support blocks 11a and 11b and the leaf springs 12a and 12b, so as to fix the column 40 in the depressed space of the heat block 10.

At the back side of the heat block 10, two heaters 21 and 22 are separately embedded along the longitudinal direction (that is, the circulation direction of the mobile phase) of the heat block 10, and two temperature sensors 31 and 32 are respectively embedded at the vicinity of the heaters 21 and 22. Hereinafter, in the two sets of the heaters and the temperature sensors, one set adjacent to an influx of the column 40 is referred to as an influx side heater 22 and an influx side temperature sensor 32, and the other set adjacent to an outflux of the column 40 is sometimes referred to as an outflux side heater 21 and an outflux side temperature sensor 31. Furthermore, each of the temperature sensors 31 and 32 is preferably disposed adjacent to one heater and distant from the other. In this way, the influence of the heat of the other heater on measuring the temperature may be reduced.

In the column oven 400, a temperature adjustment control component 410 for controlling the heating of the influx side heater 22 and the outflux side heater 21 is attached. The temperature adjustment control component 410 receives the temperature information obtained from the influx side temperature sensor 32 and the outflux side temperature sensor 31, provides heating electrical power for the influx side heater 22 and the outflux side heater 21, and adjusts the heating electrical power provided for the heaters according to detection temperatures T1 and T2 of the temperature sensors 31 and 32 and setting temperatures T1set and T2set (described below) for the heaters 21 and 22.

Furthermore, in the LC device of this embodiment, in order to perform the LC analysis, a control and processing component 600 is disposed. The control and processing component 600 wholly controls various parts, receives the detection signals from the detector 500 for processing. The control and processing component 600 is connected with an input component 700 and a display component 800, in which the input component 700 is used for specifying the analysis condition by a user; the display component 800 is used for displaying the set analysis condition, a situation of the analysis and an analysis result. The control and processing component 600 functionally has a temperature determination component 420 (equivalent to the temperature determination unit of the present invention) determining the setting temperatures T1set and T2set of the outflux side heater 21 and influx side heater 22. Generally, the control and processing component 600 is formed with a personal computer as a center, and can implement control or processing by executing a dedicated control and processing program installed in the computer.

Figure 8:
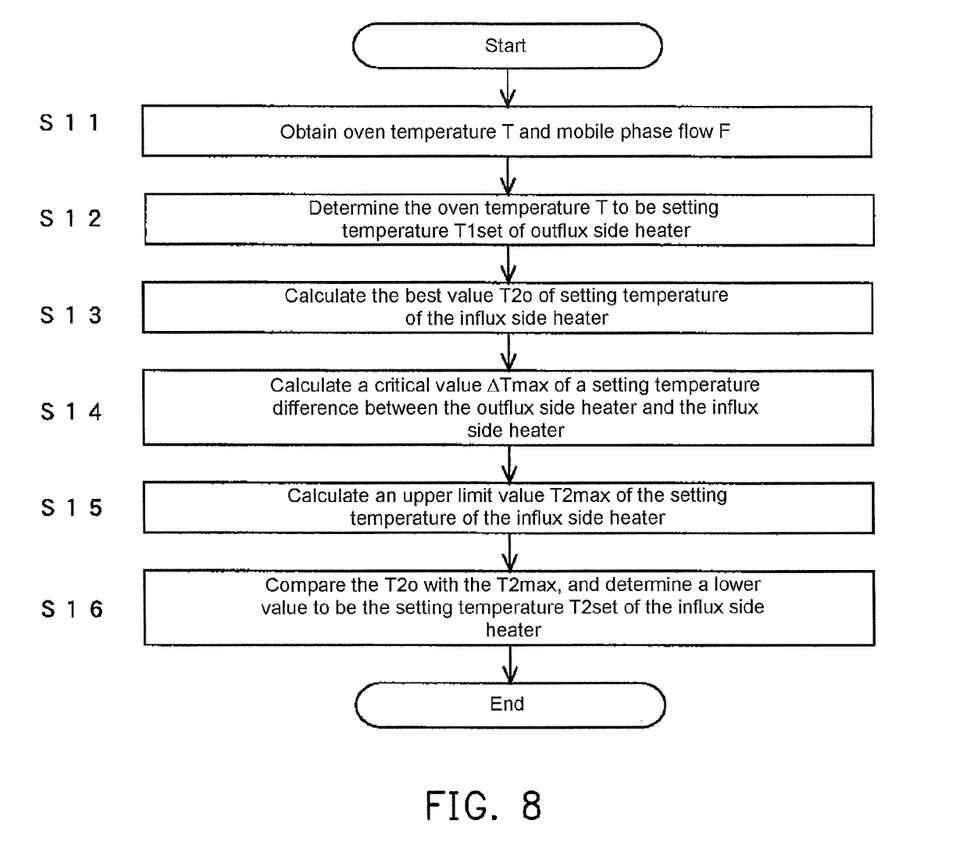
FIG. 8 is a flow chart illustrating a sequence of determining the setting temperature of the heaters in the column oven according to an embodiment.

Referring to a flow chart in FIG. 8, a determining sequence of the setting temperature T1set of the outflux side heater 21 and the setting temperature T2set of the influx side heater 22 of the temperature determination component 420 is illustrated.

Firstly, when the LC analysis starts, the user operates the input component 700 to specify the analysis condition applicable for the LC analysis. Here, the analysis condition at least includes values of the temperature of the column oven (referred as an oven temperature T below) and the flow F of the mobile phase. Furthermore, the plurality of analysis conditions may be directly specified by inputting values by the user, or indirectly specified by selecting an appropriate analysis method from a plurality of analysis methods (describing a data file of a set of analysis conditions used for performing some analysis) stored in the control and processing component 600 in advance. If a latter manner is used, values of the oven temperature T or the mobile phase flow F included in the analysis method selected by the user are specified as the oven temperature T and the mobile phase flow F in the upcoming LC analysis.

Then, the temperature determination component 420 obtains the values of the oven temperature T and the mobile phase flow F in various analysis conditions specified by the user (Step S11). Afterwards, the oven temperature T is determined to be the setting temperature T1set of the outflux side heater (Step S12).

After that, the temperature determination component 420 uses a specified formula using the oven temperature T and the mobile phase flow F as parameters to calculate the best value $T2_o$ of the setting temperature of the influx side heater (Step S13). Here, the best value $T2_o$ of the setting temperature of the influx side heater is the setting temperature of the influx side heater 22 required in a case that the temperature at the vicinity of the influx of the column 40 is substantially the same as the oven temperature T (that is, the whole column 40 has even temperature). As described above, the mobile phase with the temperature not being adjusted flows into the influx side of the column 40, and more heat is captured, so the best value $T2_O$ of the setting temperature of the influx side heater becomes a value greater than the oven temperature T. Moreover, the greater the mobile phase flow F, the more heat captured by the mobile phase, so the value of the best value $T2_O$ of the setting temperature of the influx side heater also becomes greater.

Furthermore, the temperature determination component 420 uses other formulas using the oven temperature T and the mobile phase flow F as parameters to calculate a critical value ΔTmax of a setting temperature difference between the outflux side heater and the influx side heater (Step S14). For example, if the setting temperature T2set of the influx side heater 22 is too high, the heat of the influx side heater 22 is transmitted in the column 40 and the heat block 10, and the detection temperature of the outflux side temperature sensor 31 exceeds the setting temperature T1set of the outflux side heater, so as not to perform a temperature control on the outflux side heater 21. In order to prevent this situation, in the column oven of this embodiment, a difference between the setting temperature T1set of the outflux side heater and the setting temperature T2set of the influx side heater is specified as the critical value ΔTmax. For example, when the value of the oven temperature T is small, the temperature of the heat block 10 reaches the oven temperature T through a relative low heater power, so the critical value ΔTmax of the setting temperature difference between the outflux side heater and the influx side heater becomes smaller. Furthermore, when the mobile phase flow F is great, most of the heat of the influx side heater 22 is captured by the mobile phase, so the critical value ΔTmax of the setting temperature difference between the outflux side heater and the influx side heater becomes greater. Moreover, the formulas are derived in advance through preparatory experiments and stored in the control and processing component 600.

Then, the setting temperature T1 set of the outflux side heater is added to the critical value ΔTmax of the setting temperature difference between the outflux side heater and the influx side heater, so as to calculate an upper limit value T2max of the setting temperature of the influx side heater (Step S15).

Then, the temperature determination component 420 compares the best value $T2_O$ of the setting temperature of the influx side heater with the upper limit value T2max of the setting temperature of the influx side heater which are calculated in the above manner, so as to determine a lower value to be the setting temperature T2set of the influx side heater (Step S16).

If the setting temperatures T1 set and T2set of the heaters 21 and 22 are determined in the above manner, the control and processing component 600 sends the values to the temperature adjustment control component 410 and indicates the start of the temperature adjustment control. In this way, the temperature adjustment control component 410 starts to provide electrical power for the heaters 21 and 22. Here, the temperature adjustment control component 410 adjusts the heating electrical power provided for the outflux side heater 21 according to a difference between the current temperature T1 of the heat block obtained by the outflux side temperature sensor 31 and the setting temperature T1set, and adjusts the heating electrical power provided for the influx side heater 22 according to a difference between the current temperature T2 of the heat block obtained by the influx side temperature sensor 32 and the setting temperature T2set.

Then, at a time point when the detection temperatures T1 and T2 obtained by the temperature sensors 31 and 32 respectively reach the setting temperatures T1set and T2set, the temperature adjustment control component 410 sends signals representing the situation to the control and processing component 600, and the control and processing component 600 receives the signals and controls the parts of the LC device to start the LC analysis.

Moreover, an example that the setting temperatures of the heaters are determined by the oven temperature and the mobile phase flow specified by the user is shown, but in addition, for example, the following analysis conditions may be added to determine the setting temperature of the heaters. In this situation, a formula with the following analysis conditions as parameters is established through the preparatory experiments, and the setting temperature of the heaters is determined with the formula.

(1) Room Temperature

The lower the room temperature is, the greater the heat dissipation of the heat block 10 becomes. Further, the heat generated by the influx side heater 22 is difficult to be transmitted to the outflux side, so a great setting temperature difference between the outflux side and the influx side may be obtained. Therefore, a temperature sensor used for measuring the room temperature is additionally disposed; and the critical value ΔTmax of the setting temperature difference between the outflux side heater and the influx side heater is calculated by adding a measurement value of the sensor, so as to better implement the temperature adjustment control. However, when the room temperature is low and the value of the oven temperature T specified by the user is great, and if the setting temperature difference between the outflux side and the influx side is too great (that is, the setting temperature T2set of the influx side heater 22 is too high), the setting temperature T2set may not be reached even if the power of the influx side heater 22 is always the greatest. Therefore, after the difference between the oven temperature specified by the user and the room temperature is considered, it is preferred to calculate the critical value ΔTmax of the setting temperature difference between the outflux side heater and the influx side heater.

(2) Specific Heat of Mobile Phase

The greater the specific heat of the mobile phase is, the more heat of the heat block 10 is being consumed by the mobile phase. In this way, the column temperature adjacent to the influx falls easily; hence, the setting temperature of the influx side heater 22 must be higher. That is, due to the difference of the specific heat of the mobile phase, the best value $T2_O$ of the setting temperature of the influx side heater is different. Therefore, when the best value $T2_O$ of the setting temperature of the influx side heater is determined, the temperature distribution of the column 40 is more even by adding the specific heat of the mobile phase. Furthermore, the greater the specific heat of the mobile phase is, the greater the heat dissipation of the heat block 10 is resulted; hence, a great setting temperature difference between the outflux side and the influx side may be obtained. Therefore, a better temperature adjustment control may be implemented by adding the specific heat of the mobile phase to calculate the critical value ΔTmax of the setting temperature difference between the outflux side heater and the influx side heater.

(3) Diameter of Column and Type of Filler

The heat required by the temperature adjustment of the column changes according to the diameter of the column or the type of the filler. Therefore, when the best value $T2_O$ of the setting temperature of the influx side heater and the critical value ΔTmax of the setting temperature difference between the outflux side heater and the influx side heater are calculated, a better temperature adjustment control may be implemented by adding the diameter of the column and the type of the filler.

Length of Column

The heat required by temperature adjustment of the column also changes according to the length of the column. Therefore, preferably, after the length of the column is considered, the best value $T2_O$ of the setting temperature of the influx side heater and the critical value ΔTmax of the setting temperature difference between the outflux side heater and the influx side heater are calculated. Furthermore, the length of the column may be directly input by the user using a value, but ideally, a device that automatically measures the length of the column is disposed in the column oven. As for this measurement device, for example, in the heat block 10 as shown in FIGS. 7(a) to 7(d), the support blocks 11a and 11b are constructed to slide corresponding to the length of the column 40, and the control and processing component 600 obtains an interval between two support blocks 11a and 11b, and derives the length of the column 40 according to the value of the interval.

(5) Thermal Conductivity of Mobile Phase

It is the same as other parameters, the thermal conductivity of the mobile phase may also influence the best value $T2_O$ of the setting temperature of the influx side heater and the critical value ΔTmax of the setting temperature difference between the outflux side heater and the influx side heater. Therefore, when the plurality of values is determined, a better temperature adjustment control may be implemented by adding the thermal conductivity of the mobile phase.

Furthermore, when gradient analysis is performed, the specific heat or the thermal conductivity of the mobile phase flowing into the column may change corresponding to the change of the mixing ratio of the mobile phase as time passes. Therefore, accordingly, the setting temperatures T1set and T2set of the heaters 21 and 22 preferably change in the process of implementing the analysis. Therefore, for example, the following method may be considered. The control and processing component 600 obtains an action state of the liquid delivery pump disposed for each mobile phase at a specified time interval, and derives the specific heat or the thermal conductivity of the mobile phase at the current time point according to the action state and the information of each mobile phase input in advance, and then correspondingly calculates the best value $T2_O$ of the setting temperature of the influx side heater and the critical value ΔTmax of the setting temperature difference between the outflux side heater and the influx side heater to change the setting temperatures T1set and T2set of the heaters 21 and 22. Furthermore, for example, when the composition ratio of two mobile phases A and B gradually changes, the specific heat or the thermal conductivity of the mobile phase in a plurality of states, such as a state of only the mobile phase A, a state of the composition ratio of the mobile phases A and B of 1:1, and a state of only the mobile phase B, may be logically or experimentally calculated in advance and stored in the control and processing component 600, and the setting temperatures T1set and T2set of the heaters periodically change into values appropriate for the states with the passing of the analysis time.

Figures 9A, 9B:
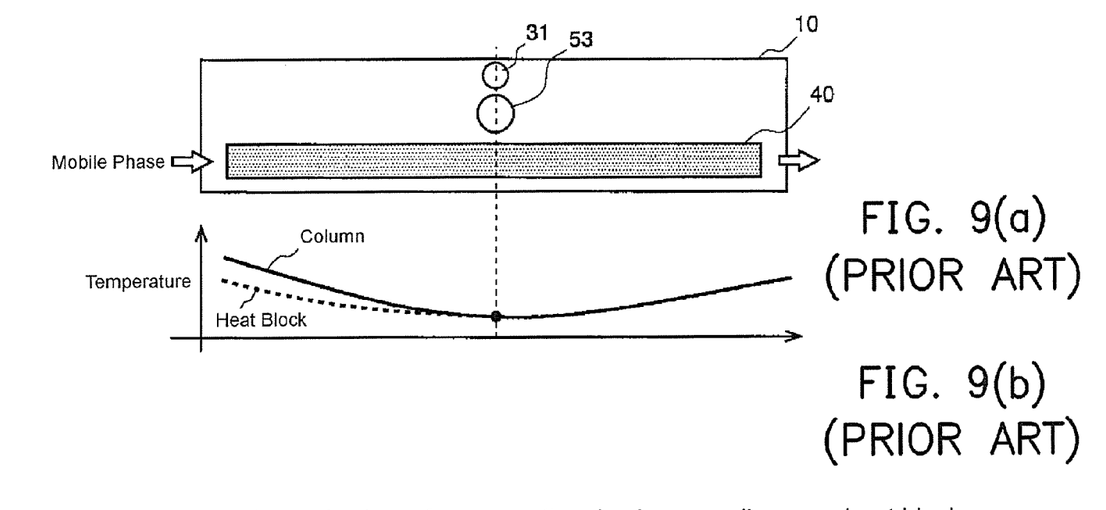
FIG. 9(a) is a schematic view of a configuration of the Pelitier Element and a temperature sensor on a heat block.
FIG. 9(b) is a diagram of the temperature distribution of the heat block and a column.
Figure 10A:
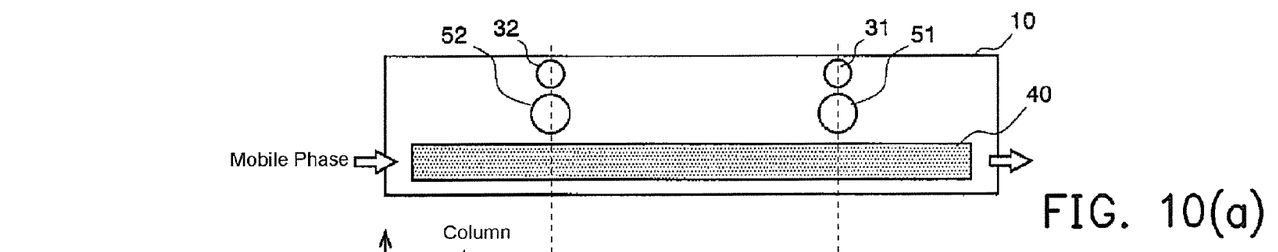
FIG. 10(a) is a schematic view of a configuration of a Pelitier Element and a temperature sensor on a heat block.
Figure 10B:
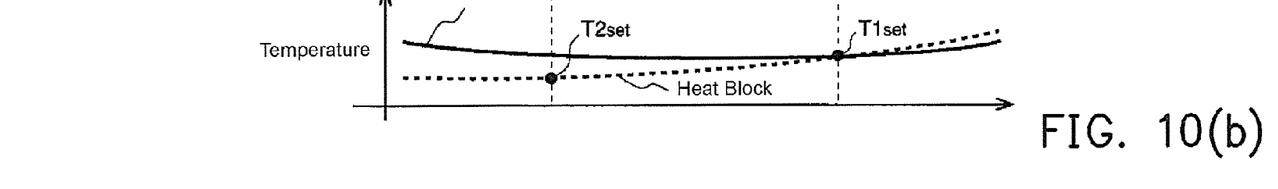
FIG. 10(b) is a diagram of the temperature distribution of the heat block and a column.

An embodiment is used to describe the pattern used for implementing the present invention above, but the present invention is not limited by the embodiment, and appropriate modifications are allowed within the theme scope of the present invention. For example, in the embodiment, a situation that the heat block is heated by using the heater is illustrated as an example; however, the present invention may also be applied in such a situation that the heat block is cooled by using the Peltier Element as the temperature adjustment body. Furthermore, generally, when the column is cooled, as shown in FIGS. 9(a) and 9(b), there is a tendency that the temperature of the influx side column is greater than the temperature of the heat block. Therefore, when the column is cooled in the column oven of the present invention, as shown in FIG. 10(a), the setting temperature T2set of the Peltier Element 52 disposed at the influx side is preferably less than the setting temperature T1set of the Peltier Element 51 disposed at the outflux side. Therefore, the column can be provided with an even temperature distribution as shown in FIG. 10(b).

Then, experiments for determining the effect of the present invention are described.

Table 1 shows results of the block temperature and the column temperature under various analysis conditions measured with the conventional column oven and the oven column of the present invention.

TABLE 1

| | Flow of Mobile Phase mL/min | Setting Temperature 1 °C. | Setting Temperature 2 °C. | Block Temperature 1 °C. | Block Temperature 2 °C. | Column Temperature (Left) °C. | Column Temperature (Centre) °C. | Column Temperature (Right) °C. | Deviation °C. |
|---|---|---|---|---|---|---|---|---|---|
| Experiment Example 1 | 0.5 | 50 | — | 50.00 | — | 48.3 | 50.3 | 50.5 | 2.2 |
| Experiment Example 2 | 1 | 50 | — | 50.00 | — | 48.5 | 50.1 | 50.4 | 1.9 |
| Experiment Example 3 | 0.5 | 50 | 51.37 | 50.00 | 51.37 | 50.01 | 49.84 | 49.28 | 0.73 |
| Experiment Example 4 | 1 | 50 | 51.71 | 50.00 | 51.71 | 50.52 | 50.42 | 49.74 | 0.78 |

As shown in FIGS. 11(a) and 11(b), Experiment Examples 1 and 2 are the exemplary experiments in which the temperature is adjusted through a heater 71 and a temperature sensor 81 disposed at one place of the central part of a heat block 60, which are equivalent to the prior art. As shown in FIGS. 3(a) and 3(b), Experiment Examples 3 and 4 are the exemplary experiments in which the temperature is adjusted through the heaters 21 and 22 and the temperature sensors 31 and 32 disposed at two places of the outflux side and the influx side of the heat block 10 respectively, and a difference is set between the setting temperatures of the influx side heater 22 and the outflux side heater 21.

In the table, under the columns of "column temperature (left)", "column temperature (center)", and "column temperature (right)", the surface temperatures of the columns at the vicinity of the influx side, the central place, and the vicinity of the outflux side of the columns 90 and 40 are respectively presented. In Exemplary Experiment 1 and 2, "setting temperature 1" and "block temperature 1" are respectively the setting temperature of the heater 71 and the detection temperature of the temperature sensor 81. In Exemplary Experiments 3 and 4, "setting temperature 1" and "block temperature 1" are respectively the setting temperature of the outflux side heater 21 and the detection temperature of the outflux side temperature sensor 31, and "setting temperature 2" and "block temperature 2" are respectively the setting temperature of the influx side heater 22 and the detection temperature at the influx side temperature sensor 32. Furthermore, the Exemplary Experiments 1 to 4 are all performed at the room temperature of 25° C.

It can be understood from the table that, comparing to the exemplary experiments (Exemplary Experiments 1 and 2), in which the temperature is normally adjusted for only one place, the evenness of the column temperature of the exemplary experiments (Experiment Examples 3 and 4), in which the temperature is adjusted for two places and the setting temperature at the influx side is higher than that at the outflux side, is determined to have improved.

Table 2 shows results of the block temperature and the column temperature under various analysis conditions measured by using the column oven of the present invention.

downstream side of the heat block, and the difference is set between the setting temperatures of the influx side heater 22 and the outflux side heater 21. Exemplary Experiments 14 to 18 are experiment in which the critical value ΔTmax is set for the setting temperature difference between the outflux side heater and the influx side heater as shown in FIGS. 5(a) and 5(b).

In the Table, the columns of "setting temperature 1", "setting temperature 2", "block temperature 1", and "block temperature 2" represent the same parameters as those in Exemplary Experiments 3 and 4 in Table 1; and under the column "heater power 1" the power of the outflux side heater 21 is presented, and under the column "heater power 2", the power of the influx side heater 22 is presented.

Similarly for the Exemplary Experiments 5 to 8, when the setting temperature is close to the room temperature, the power of the heater is not required; hence, if the setting temperature of the influx side heater is too high (that is, if the setting temperature difference between the outflux side and the influx side is too great), the block temperature at the outflux side is higher than the setting temperature due to the influence of the temperature at the influx side. In this situation, the power of the outflux side heater is 0%, and the temperature adjustment control of the outflux side heater can not be used. The Exemplary Experiments 14 and 15 are the experiments in which the critical value ΔTmax is set for the setting temperature difference between the outflux side heater and the influx side heater on the basis of a plurality of data; therefore, it can be known that the power of the heater is not 0% so as to implement the temperature adjustment control by using two heaters, even if the room temperature is close to the setting temperature.

TABLE 2

| | Room Temperature ° C. | Flow of Mobile Phase mL/min | Setting Temperature 1 ° C. | Setting Temperature 2 ° C. | Block Temperature 1 ° C. | Block Temperature 2 ° C. | Heater Power 1 % | Heater Power 2 % |
|---|---|---|---|---|---|---|---|---|
| Experiment Example 5 | 35 | 2 | 40 | 41 | 40.31 | 41.00 | 0 | 2 |
| Experiment Example 6 | 35 | 2 | 40 | 42 | 41.17 | 42.00 | 0 | 3 |
| Experiment Example 7 | 35 | 2 | 50 | 52 | 50.00 | 52.00 | 0 | 9 |
| Experiment Example 8 | 35 | 2 | 50 | 53 | 50.66 | 53.00 | 0 | 10 |
| Experiment Example 9 | 35 | 2 | 100 | 108 | 100.00 | 108.00 | 4 | 45 |
| Experiment Example 10 | 35 | 2 | 100 | 109 | 100.00 | 109.00 | 2 | 47 |
| Experiment Example 11 | 4 | 3 | 100 | 109 | 100.00 | 109.00 | 13 | 65 |
| Experiment Example 12 | 4 | 3 | 150 | 158 | 150.00 | 158.00 | 34 | 87 |
| Experiment Example 13 | 4 | 3 | 150 | 160 | 150.00 | 160.00 | 29 | 92 |
| Experiment Example 14 | 35 | 2 | 40 | 40.36 | 40.00 | 40.36 | 1 | 3 |
| Experiment Example 15 | 35 | 2 | 50 | 51.82 | 50.00 | 51.82 | 1 | 12 |
| Experiment Example 16 | 35 | 2 | 100 | 106.15 | 100.00 | 106.15 | 5 | 54 |
| Experiment Example 17 | 4 | 2 | 100 | 106.15 | 100.00 | 106.15 | 16 | 70 |
| Experiment Example 18 | 4 | 2 | 150 | 155.47 | 150.00 | 155.47 | 34 | 89 |

Experiment Examples 5 to 18 are the experiments in which the temperature is adjusted by the heater and temperature sensor disposed at two places of the upstream side and the Furthermore, as described above, when the oven temperature (the same as the setting temperature of the outflux side heater here) specified by the user is too high relative to the room temperature, if the setting temperature difference between the outflux side heater and the influx side heater becomes greater, a possibility that even if the power of the influx side heater is set to be 100%, the setting temperature can not be reached. Therefore, Exemplary Experiments 17 and 18 are the experiments in which the critical value $\Delta Tmax$ of the setting temperature difference between the outflux side heater and the influx side heater is determined by adding a difference between the room temperature and the oven temperature, and the setting temperature of the influx side heater is determined by applying the critical value $\Delta Tmax$. According to the examples, comparing with a situation that the critical value is not applied (Experiment Examples 11, 12, and 13), the power of the influx side heater is controlled.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A column oven, for heating or cooling one heat block contacting a column, and adjusting a temperature of the column through heat transmission from the heat block, the one heat block having a longitudinal direction of from an influx of the column to an outflux of the column, and the column oven comprising:
   a) a plurality of temperature adjustment bodies, separately disposed along the longitudinal direction of the heat block, and heating or cooling the heat block;
   b) a plurality of temperature sensors, measuring temperatures of the heat block adjacent to the temperature adjustment bodies;
   c) a control unit, controlling the corresponding temperature adjustment bodies independently according to the temperatures of the heat block measured by the temperature sensors; and
   d) a temperature determination unit, respectively determining setting temperatures of temperature adjustment bodies according to an analysis condition that at least comprises a temperature of the column oven and a flow of a mobile phase applied in an analysis,
   wherein
   the control unit controls the temperature adjustment bodies in a manner of enabling the temperatures measured by the temperature sensors to reach the setting temperatures of the temperature adjustment bodies,
   the temperature determination unit determining the setting temperatures of the plurality of temperature adjustment bodies comprises: when the heat block is heated through the temperature adjustment bodies, the setting temperature of the temperature adjustment body disposed nearer to the influx of the column becomes higher, and
   the temperature determination unit derives a critical value of a setting temperature difference of the temperature adjustment bodies according to the analysis condition, and determines the setting temperatures of the temperature adjustment bodies in a manner such that the setting temperature difference of the temperature adjustment bodies is smaller than the critical value.

2. The column oven according to claim 1, wherein:
   the temperature determination unit further incorporates at least any one of a room temperature, a specific heat of the mobile phase, a thermal conductivity of the mobile phase, a diameter of the column, a type of a filler of the column, a length of the column to be the analysis condition to determine the setting temperatures of the temperature adjustment bodies.

3. A column oven, for heating or cooling one heat block contacting a column, and adjusting a temperature of the column through heat transmission from the heat block, the one heat block having a longitudinal direction of from an influx of the column to an outflux of the column, and the column oven comprising:
   a) a plurality of temperature adjustment bodies, separately disposed along the longitudinal direction of the heat block, and heating or cooling the heat block;
   b) a plurality of temperature sensors, measuring temperatures of the heat block adjacent to the temperature adjustment bodies;
   c) a control unit, controlling the corresponding temperature adjustment bodies independently according to the temperatures of the heat block measured by the temperature sensors; and
   d) a temperature determination unit, respectively determining setting temperatures of temperature adjustment bodies according to an analysis condition that at least comprises a temperature of the column oven and a flow of a mobile phase applied in an analysis,
   wherein
   the control unit controls the temperature adjustment bodies in a manner of enabling the temperatures measured by the temperature sensors to reach the setting temperatures of the temperature adjustment bodies,
   the temperature determination unit determining the setting temperatures of the plurality of temperature adjustment bodies comprises: when the heat block is heated through the temperature adjustment bodies, the setting temperature of the temperature adjustment body disposed nearer to the influx of the column becomes higher, and when the heat block is cooled through the temperature adjustment bodies, the setting temperature of the temperature adjustment body disposed nearer to the influx of the column becomes lower,
   the temperature determination unit derives a critical value of a setting temperature difference of the temperature adjustment bodies according to the analysis condition, and determines the setting temperatures of the temperature adjustment bodies in a manner such that the setting temperature difference of the temperature adjustment bodies is smaller than the critical value, and
   the temperature determination unit determines the setting temperatures of the temperature adjustment bodies and derives the critical value such that a temperature difference between the influx of the column and the outflux of the column is minimized.

* * * * *